United States Patent [19]
Drake

[11] Patent Number: 6,042,802
[45] Date of Patent: Mar. 28, 2000

[54] METHOD AND APPARATUS FOR GENERATING AND USING CHLORINE DIOXIDE

[75] Inventor: James Franklin Drake, Minneapolis, Minn.

[73] Assignee: Medivators Inc., Eagan, Minn.

[21] Appl. No.: 08/950,697

[22] Filed: Oct. 15, 1997

[51] Int. Cl.$^7$ ................................................ C01B 11/02
[52] U.S. Cl. .................... 423/477; 423/240 R; 422/37
[58] Field of Search .................. 423/240, 241, 423/472, 477; 422/37; 216/93, 84; 156/345 LC

[56] References Cited

U.S. PATENT DOCUMENTS

| | | |
|---|---|---|
| 4,013,761 | 3/1977 | Ward et al. . |
| 4,250,144 | 2/1981 | Ratigan . |
| 4,862,872 | 9/1989 | Yabe et al. . |
| 5,066,477 | 11/1991 | Zell et al. . |
| 5,110,580 | 5/1992 | Rosenblatt et al. ............. 423/477 X |
| 5,227,306 | 7/1993 | Eltomi et al. . |
| 5,234,678 | 8/1993 | Rosenblatt et al. . |
| 5,246,662 | 9/1993 | Ripley et al. . |
| 5,290,524 | 3/1994 | Rosenblatt et al. . |
| 5,326,546 | 7/1994 | Rosenblatt et al. . |
| 5,380,518 | 1/1995 | Roozdar . |
| 5,407,656 | 4/1995 | Roozdar . |
| 5,618,440 | 4/1997 | Mason ................................. 423/477 X |
| 5,656,248 | 8/1997 | Kline et al. . |

FOREIGN PATENT DOCUMENTS

| | | |
|---|---|---|
| 0 847 759 A2 | 6/1998 | European Pat. Off. . |
| 3712-701 | 10/1987 | Germany . |
| 4102-055 | 8/1991 | Germany . |
| 5-95901 | 4/1993 | Japan . |
| 5-253183 | 10/1993 | Japan . |
| WO 8604698 | 8/1986 | WIPO . |

OTHER PUBLICATIONS

Kirk–Othmer, "Encyclopedia of Chemical Technology", 4th ed., vol. 5, Carbon and Graphite Fibers to Chlorocarbons and Chlorohydrocarbons–$C_1$, pp. 968–997 (1993).

*Primary Examiner*—William Powell
*Attorney, Agent, or Firm*—Merchant & Gould P.C.

[57] ABSTRACT

The present disclosure relates to a method for generating a volume of chlorine dioxide based sterilant/disinfectant. The method includes the step of generating chlorine dioxide gas, and transferring the chlorine dioxide gas to a sterilization chamber. It also includes the step of monitoring the concentration of chlorine dioxide gas within the sterilization chamber, and terminating the transfer of chlorine dioxide gas to the sterilization chamber when the concentration of chlorine dioxide within the chamber reaches a predetermined level.

20 Claims, 3 Drawing Sheets

METHOD AND APPARATUS FOR GENERATING AND USING CHLORINE DIOXIDE

FIELD OF THE INVENTION

The present invention relates generally to methods and apparatuses for generating and using chlorine dioxide. More specifically, the present invention relates to methods and apparatuses for generating chlorine dioxide for use in disinfecting or sterilizing objects such as medical instruments.

BACKGROUND OF THE INVENTION

Chlorine dioxide is known to have bleaching, disinfecting and sterilizing properties. Another significant property of chlorine dioxide is that it is not stable for long periods of time. Consequently, chlorine dioxide is typically used in large scale industrial applications where the chlorine dioxide can be used shortly after it has been generated. Common uses for chlorine dioxide include bleaching paper and flour, and disinfecting municipal water supplies.

Chlorine dioxide has also been used at a smaller scale in places such as hospitals to sterilize or disinfect medical instruments and devices. In hospital applications, chlorine dioxide has been generated by mixing a sodium chlorite solution with an organic acid solution. By mixing the sodium chlorite solution with the organic acid solution, a disinfectant solution is generated. The disinfectant solution, which includes small amounts of sodium chloride, as well as residual sodium chlorite and residual organic acids, is used for disinfection or sterilization purposes within the hospital setting.

The use of chlorine dioxide for hospital applications, as described above, is problematic for several reasons. First, the process has relatively low yields of chlorine dioxide. Hence, the process is relatively expensive. Also, both sodium chlorite and organic acids have corrosive qualities. As a result, the disinfectant solution described above also has corrosive effects which can be harmful when used to disinfect objects such as medical equipment.

What is needed is a method and apparatus for efficiently generating chlorine dioxide in relatively small scales at a local level. What is also needed is a method and apparatus for efficiently generating non-corrosive chlorine dioxide solutions for use as a disinfectant in settings such as hospitals, restaurants, stores, or any other place an environmentally friendly and safe disinfectant is needed. What is further needed is a method and apparatus for rapidly transferring chlorine dioxide gas to a solution in a controlled manner. The present invention addresses the above described needs as well as other needs.

SUMMARY

One aspect of the present invention relates to a method for generating a volume of disinfectant/sterilant fluid having a predetermined concentration of chlorine dioxide. The method includes the step of generating chlorine dioxide gas at a source of chlorine dioxide gas. The method also includes the steps of tranferring the chlorine dioxide gas from the source of chlorine dioxide gas into a chamber, and monitoring the concentration of chlorine dioxide in the chamber. The method further includes the step of discontinuing the transfer of chlorine dioxide gas to the chamber when the concentration of chlorine dioxide in the chamber reaches the predetermined concentration.

Another aspect of the present invention relates to a method for generating a volume of disinfectant/sterilant liquid having a predetermined concentration of chlorine dioxide. The method includes the step of generating chlorine dioxide gas at a source of chlorine dioxide gas. The method also includes the steps of tranferring the chlorine dioxide gas from the source of chlorine dioxide gas into a separate chamber, and dissolving at least a portion of the chlorine dioxide gas into a solvent contained in that chamber. The method additionally includes the step of monitoring the concentration of chlorine dioxide dissolved within the solvent in the chamber. Finally, the method includes the step of discontinuing the transfer of chlorine dioxide gas to the chamber when the concentration of chlorine dioxide gas dissolved in the chamber reaches the predetermined concentration.

A further aspect of the present invention relates to a method for disinfecting or sterilizing a medical instrument. In practicing the method, the medical instrument is placed in a disinfecting/sterilizing chamber. Chlorine dioxide gas is then generated at a source of chlorine dioxide gas and transferred to the chamber. As the chlorine dioxide gas is transferred to the chamber, the concentration of chlorine dioxide within the chamber is monitored. Once the concentration of chlorine dioxide within the chamber reaches a predetermined concentration suitable for disinfecting or sterilizing the medical instrument, the transfer of chlorine dioxide gas to the chamber can be discontinued. After the medical instrument has been exposed to the predetermined concentration of chlorine dioxide for a predetermined period suitable for disinfecting or sterilizing the medical instrument, the medical instrument can be removed from the chamber. It will be appreciated that the medical instrument can be placed in the chamber either before or after the chamber reaches the predetermined concentration of chlorine dioxide. Furthermore, for certain applications, the sterilant/disinfectant within the chamber can be dispensed from the chamber and used for disinfecting or sterilizing purposes at remote locations.

Still another aspect of the present invention relates to an apparatus for generating a volume of disinfectant/sterilant fluid having a predetermined concentration of chlorine dioxide. The apparatus includes a chlorine dioxide generator for generating chlorine dioxide gas. The apparatus also includes a disinfectant chamber separate from the chlorine dioxide generator, and a flow path for transferring chlorine dioxide gas from the generator to the disinfectant chamber. The apparatus further includes a concentration sensor for monitoring the concentration of chlorine dioxide in the chamber, and means for discontinuing the transfer of chlorine dioxide gas to the chamber when the concentration of chlorine dioxide within the chamber reaches a predetermined level.

The various aspects of the present invention provide methods and apparatuses for efficiently generating relatively small quantities of chlorine dioxide gas for use as a disinfectant/sterilant at places such as stores, hospitals, restaurants or any other place a safe, environmentally friendly disinfectant is needed. The present invention also provides methods and apparatuses for efficiently generating a non-corrosive chlorine dioxide based disinfectant/sterilant suitable for disinfecting or sterilizing objects such as medical instruments. The present invention further provides methods and apparatuses for rapidly transferring chlorine dioxide gas to a solution in a controlled manner.

A variety of additional advantages of the invention will be set forth in part in the description which follows, and in part will be apparent from the description, or may be learned by practicing the invention. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several aspects of the invention and together with the description, serve to explain the principles of the invention. A brief description of the drawings is as follows.

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

Figure 1:
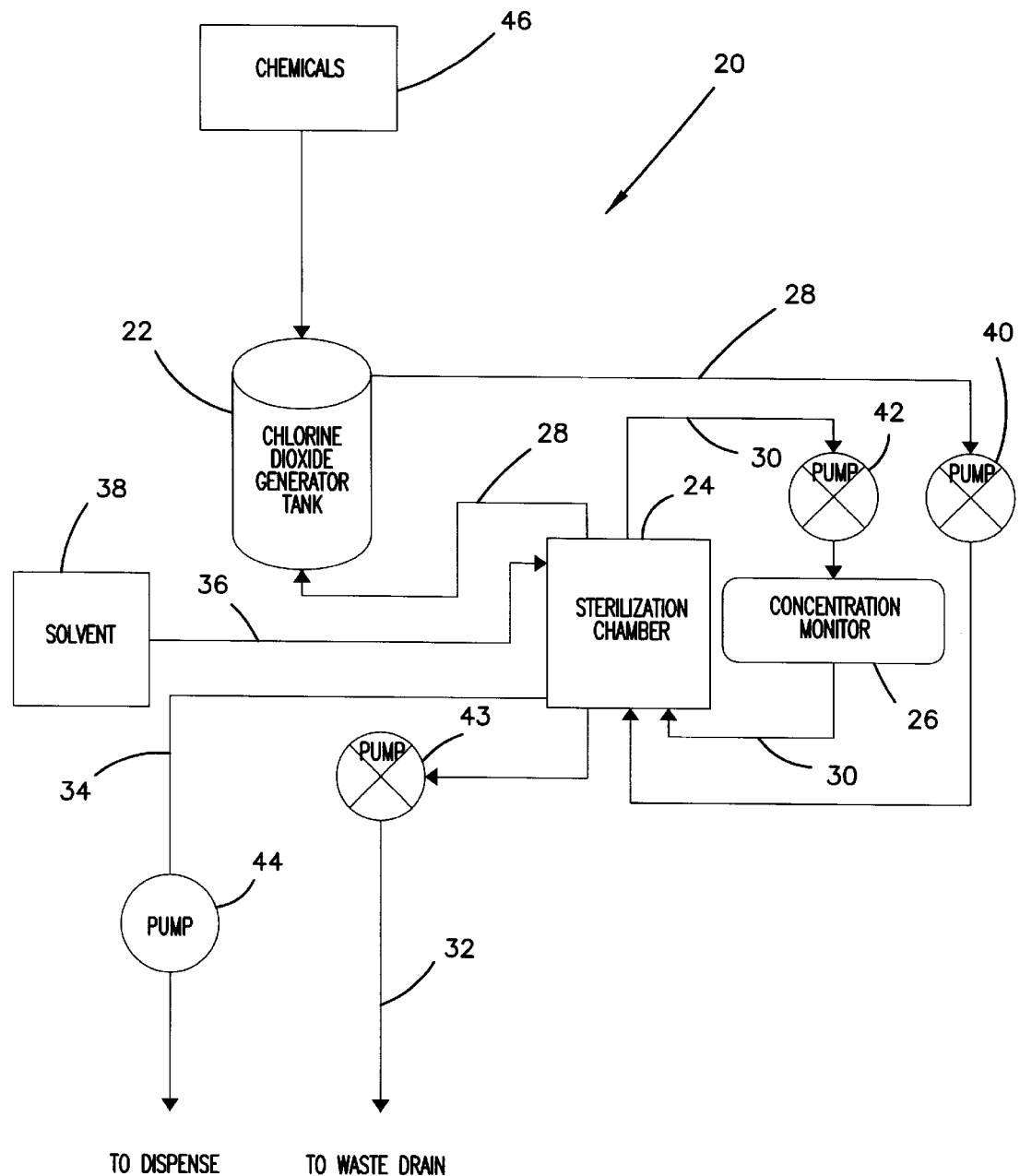
FIG. 1 is a schematic diagram of a sterilant/disinfectant generator constructed in accordance with the principles of the present invention.

FIG. 1 is a schematic diagram of a sterilizing/disinfecting system 20 constructed in accordance with the principles of the present invention. Generally, the system 20 includes a chlorine dioxide generator 22, a sterilization/disinfecting chamber 24 (hereinafter "sterilization chamber 24") and a chlorine dioxide concentration monitor 26. A first fluid flow line 28 forms a closed loop between the generator 22 and the sterilization chamber 24. A second fluid flow line or path 30 forms a closed loop between the sterilization chamber 24 and the concentration monitor 26. The system 20 further includes a third fluid flow line 32 for discharging spent sterilant/disinfectant from the sterilization chamber 24, a fourth fluid flow line 34 for dispensing active sterilant/disinfectant from sterilization chamber 24, and a fifth fluid flow line 36 for supplying solvent from a solvent source 38 to the sterilization chamber 24. First, second, third and fourth pumps 40, 42, 43 and 44 respectively control fluid flow through the first, second, third and fourth flow lines 28, 30, 32 and 34.

The chlorine dioxide generator 22 of the system 20 is shown as a tank configured to receive chemicals from a chemical source 46. The chemicals provided to the chlorine dioxide generator 22 are adapted to chemically react with one another so as to generate a quantity of chlorine dioxide gas. Those skilled in the art will recognize that chlorine dioxide gas can be generated by many well-known chemical reactions. For example, chlorine dioxide can be generated by combining chlorates with acids or reducing agents, or by combining chlorites with chlorine, hypochlorite, aldehydes acids, or acid anhydrides. Of course, a variety of other chemical reactions can also be used to generate chlorine dioxide. Although the present invention could utilize any of the known techniques for generating chlorine dioxide gas, it is preferred to generate chlorine gas by mixing sodium chlorite with hydrochloric acid as shown by the following chemical equation:

$$5\ NaClO_2 + 4\ HCl \rightarrow 4\ ClO_2 + 5\ NaCl + 2\ H_2O$$

Figure 2:
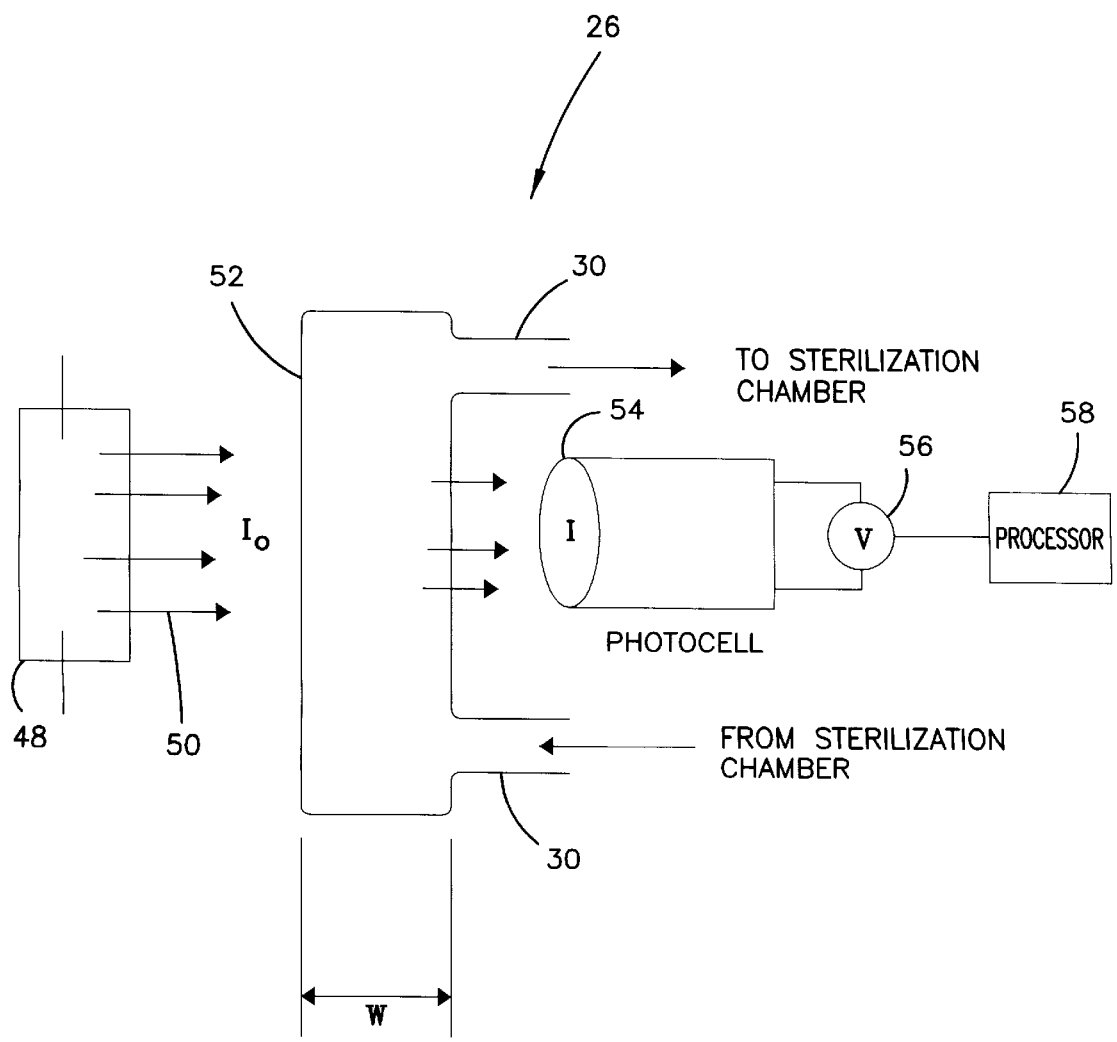
FIG. 2 is a schematic diagram of an exemplary chlorine dioxide concentration monitor used in association with the system of FIG. 1.

The chlorine dioxide concentration monitor 26 of the system 20 is used to sense the concentration of chlorine dioxide in the sterilization chamber 24. FIG. 2 shows a schematic diagram of an exemplary version of the monitor 26 which is capable of sensing the concentration of chlorine dioxide in a liquid or gas. The concentration monitor 26 includes an ultraviolet light source 48 that is capable of producing light 50 preferably having a wave length of approximately 360 nanometers. The monitor 26 also includes a transparent chamber 52 positioned along the second flow line 30. The chamber 52 is configured such that the light source 48 can direct the light 50 through a width w of the chamber 52. The monitor 26 also includes a photocell 54 for measuring the intensity of light that passes from the UV light source 48 through the transparent chamber 52. The electrical output of the photocell 54 is proportional to the intensity of the light falling on the photocell 54 over a wide range of intensities.

To measure the concentration of chlorine dioxide in the sterilization chamber 24, fluid from the sterilization chamber 24 is continuously circulated through the transparent chamber 52 via the second flow line 30. As the fluid containing chlorine dioxide passes through the transparent chamber 52, the UV light source 48 projects the light 50 through the fluid within the transportation chamber 52. The photocell 54 measures the intensity of the beam that passes through the chlorine dioxide containing fluid within the chamber 52. Using a variation of the Beer-Lambert Law, the concentration C (moles/liter) of chlorine dioxide within the fluid through which the light 50 passes can be calculated by the formula:

$$C = \log\left(\frac{I_0}{I}\right) / (\alpha w)$$

In the formula, $\alpha$ is a constant representative of the given absorbing material, in this case chlorine dioxide in water. The value of $\alpha$ for chlorine dioxide in water is 1100 liters/mole-cm. Additionally, $I_o$ is the intensity of the light 50 before it passes through the transparent chamber 52 and I is the intensity of the light after it passes through the transparent chamber 52. Finally, w is the width of the transparent chamber 52.

$I_o$ can be determined by measuring the intensity of light falling on the photocell 54 when only water is flowing through the transparent chamber 52. The intensity I is determined by measuring the intensity of light falling on the photocell when fluid drawn from the sterilization chamber 24 is flowing through the transparent chamber 52. It will be appreciated that the photocell 54 interfaces with known circuitry 56 suitable for measuring the electrical output of the photocell 54. The electrical circuitry 56 in turn interfaces with a known processor 58 adapted to calculate the concentration of chlorine dioxide in the transparent chamber 52 based on the electrical output provided by the photocell 54. The processor 58 also includes suitable control logic for controlling the first, second, third and fourth pumps 40, 42, 43 and 44. Consequently, when the concentration of chlorine dioxide within the sterilization chamber 24 reaches a predetermined level, the processor 58 can be programmed to deactivate the first and second pumps 40 and 42.

Referring back to FIG. 1, the solvent source 38 can provide any type of solvent suitable for dissolving chlorine dioxide. Exemplary solvents include water, organic solvents, alcohols, and chlorinated solvents. Those skilled in the art will appreciate that other solvents can also be utilized.

To generate sterilant/disinfectant (hereafter "sterilant") in the sterilization chamber 24, the sterilization chamber 24 is first filled with solvent from the solvent source 38. Next, chlorine dioxide gas is generated in the generator 22 by adding suitable chemicals from the chemical source 46 to the generator 22. Once chlorine dioxide gas has been generated in the generator 22, the first and second pumps 40 and 42 are activated. The first pump 40 causes a mixture of air and chlorine dioxide to be drawn through the first flow line 28 to the sterilization chamber 24. The mixture of air and chlorine dioxide are bubbled through the solvent within the sterilization chamber 24. As the mixture of air and chlorine dioxide bubble through the solvent, chlorine dioxide is dissolved within the solvent. Air and small concentrations of chlorine dioxide are circulated from the sterilization chamber 24 back to the chlorine dioxide generator 22 through the first flow line 28.

The second pump 42 continuously circulates the solvent containing the dissolved chlorine dioxide from the sterilization chamber 24 past the concentration monitor 26. Consequently, the concentration monitor 26 constantly monitors the concentration of chlorine dioxide within the sterilization chamber 24. The concentration of chlorine dioxide will steadily increase within the sterilization chamber 24 as the chlorine dioxide is transferred from the generator 22 through the first flow line 28 to the sterilization chamber 24. Once the concentration of chlorine dioxide within the sterilization chamber 24 reaches a predetermined concentration, such predetermined concentration is detected by the concentration monitor 26 and the first and second pumps 40 and 42 are deactivated. It is preferred for the resultant sterilant in the sterilization chamber 24 to have a chlorine dioxide concentration in the range of 20 to 1,000 parts per million (ppm).

Once the desired concentration of chlorine dioxide is reached within the sterilization chamber 24, the sterilant contained within the sterilization chamber 24 is ready for use. For example, the sterilant can be dispensed from the sterilization chamber 24 via the fourth flow line 34. The sterilant dispensed from the fourth flow line 34 can be used to sanitize, disinfect, or sterilize a variety of products. For example, the sterilant can be used to disinfect or sterilize hard surfaces such as countertops, dishes, bowls, sinks and floors. Furthermore, the sterilant can be used to sanitize edibles such as vegetables. Moreover, the sterilant can be used to sterilize medical instruments or to sanitize hands prior to surgical procedures.

It will be appreciated that objects can also be sterilized or disinfected directly within the sterilization chamber 24. For example, prior to generating sterilant, medical instruments such as rigid or flexible endoscopes, surgical instruments, lenses, or ophthalmic instruments can be placed within the sterilization chamber 24. The system 20 is then used, as described above, to generate a sterilant within the sterilization chamber 24. The sterilant bathes the objects desired to be sterilized and has a concentration of chlorine dioxide suitable for sterilizing such objects. A preferred sterilization/disinfection time is in the range of 5 minutes to 60 minutes. Throughout the sterilization/disinfection process, the concentration of chlorine dioxide within the sterilization chamber 24 can be monitored by the concentration monitor 26. If the concentration of chlorine dioxide falls below a predetermined level, additional chlorine dioxide gas can be transferred from the generator 22 to the sterilization chamber 24. After the sterilization process, the spent sterilant is removed from the sterilization chamber 24 through the third flow line 32 and the sterilized/disinfected objects can be removed from the sterilization chamber 24.

It will also be appreciated that the use of solvent within the sterilization chamber is strictly optional. For certain applications, it may be desirable to sterilize/disinfect objects within the sterilization chamber 24 via gaseous chlorine dioxide that is not in liquid solution. To utilize gaseous chlorine dioxide as a sterilant, the system 20 is used in the same way described above except that no liquid solvent is provided to the sterilization chamber 24. When the first pump is activated, chlorine dioxide is transferred from the generator 22 to the sterilization chamber 24 as the sterilization chamber 24 and the generator 22 move towards equilibrium. As discussed above, the concentration monitor deactivates the first pump 40 when the concentration of chlorine dioxide within the sterilization chamber 24 reaches a predetermined level. For some uses, the sterilization chamber 24 can be evacuated prior to transferring chlorine dioxide to the chamber 24.

It is significant that the generator 22 and the sterilization chamber 24 are separate from one another. Chlorine dioxide, which is relatively volatile, is transferred from the generator 22 to the sterilization chamber 24 via the first flow line 28. In contrast, acids and chlorite, which are not relatively volatile, primarily remain within the generator 22. As a result, the sterilant generated within the sterilization chamber 24 is substantially free of corrosive chemicals. Furthermore, in utilizing the system 20, it is not necessary to maintain a precise quantitative control over the chemicals used to generate the chlorine dioxide gas. Precise control is not required because the actual concentration of chlorine dioxide in the sterilant is precisely and continuously monitored by the concentration monitor 26. Consequently, excess chlorine dioxide can be generated without any adverse effect.

Figure 3:
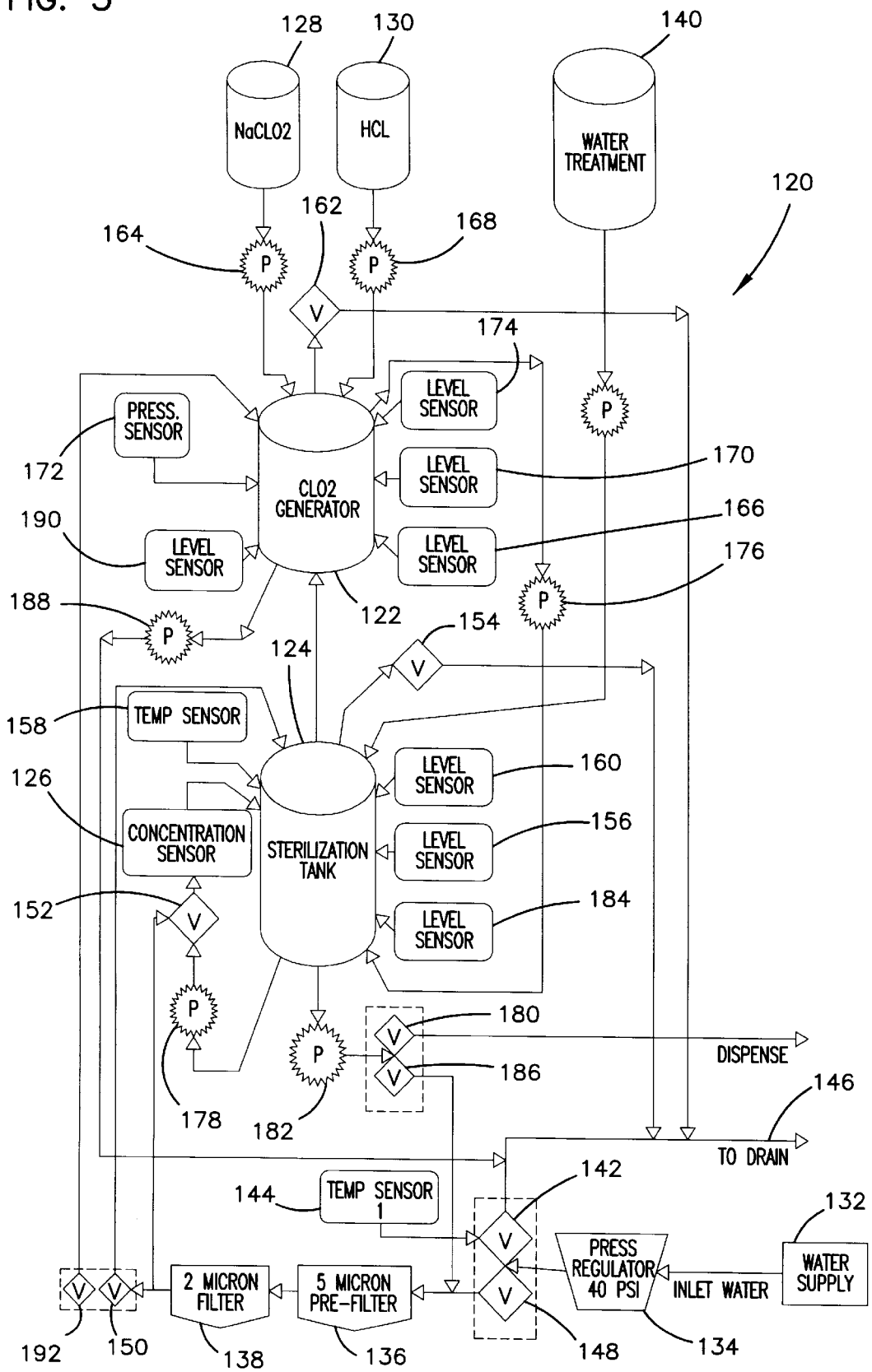
FIG. 3 is a more detailed schematic diagram of another chlorine dioxide sterilant/disinfectant generator that is constructed in accordance with the principles of the present of the present invention.

FIG. 3 is a more detailed system 120 for generating sterilant/disinfectant that operates in much the same manner as the system 20 of FIG. 1. Generally, the system 120 includes a chlorine dioxide generator tank 122, a sterilization/disinfection tank 124 (hereinafter "sterilization tank 124"), and a chlorine dioxide concentration monitor 126 for monitoring the concentration of chlorine dioxide in the sterilization tank 124. Chemicals for generating chlorine dioxide are supplied to the chlorine dioxide generator 122 by a source of sodium chlorite 128 and a source of hydrochloric acid 130. The system 120 is designed to use water as a chlorine dioxide solvent and is connected to a water supply 132. A pressure regulator 134 controls the pressure of water entering the system 120, while first and second filters 136 and 138 purify the water before it is used within the system 120. The system 120 further includes a source of water treatment chemicals 140 that can selectively be added to the sterilization tank 124. Exemplary water and chemicals include anticorrosion additives, surfactants, water softeners and water conditioners.

In use of the system 120, the sterilization tank 124 is first filled with water from the water supply 132. The sterilization tank 124 filling process begins with the opening of valve 142. When valve 142 is opened, water is directed past temperature sensor 144 to a drain 146. Temperature sensor 144 monitors the water temperature to verify that it is within a predetermined temperature range. A preferred temperature range is between 25° C. and 45° C. If the water temperature is not within the predetermined temperature range, an alarm will sound and the filling process will stop. Alternatively, if the water temperature is within the predetermined range, valve 142 is closed and fill valves 148, 150, and 152 are opened such that the sterilization tank 124 begins to fill with water. Vent valve 154 is also opened so that air is allowed to vent from the sterilization tank 124 as the tank fills with water.

The main supply of water to the sterilization tank 124 flows through valve 150, while a smaller amount of water flows through valve 152 past the chlorine dioxide monitor 126. As the water flows past the concentration monitor 126, the concentration monitor 126 takes a reference reading based on the water to verify that the concentration sensor is operating properly. The sterilization tank 124 continues to fill until the water reaches level sensor 156. When level sensor 156 is activated, valves 150, 152, and 154 are closed, and tank temperature sensor 158 verifies the temperature in the tank 124. As a safety feature, the sterilization tank 124 is also equipped with an overflow sensor 160 for terminating water flow to the sterilization tank 124 in the event that level sensor 156 fails.

After the sterilization tank 124 has been filled with water and the water temperature verified, the chlorine dioxide generation process is initiated by opening vent valve 162 and activating pump 164. Pump 164 transfers sodium chlorite to the chlorine dioxide generator 122, while vent valve 162 vents air from the generator 122 to the atmosphere. The generator 122 is filled with sodium chlorite to level sensor 166. When level sensor 166 is activated, pump 164 is deactivated and pump 168 is activated such that hydrochloric acid is transferred to the generator tank 122. Pump 168 continues to pump hydrochloric acid into the generator 122 until the generator is filled to level sensor 170. When level sensor 170 is activated, vent valve 162 is closed and pump 168 is deactivated.

The combination of sodium chlorite and hydrochloric acid in the generator tank 122 initiates the production of chlorine dioxide gas within the generator 122. Pressure within the tank 122 is monitored by pressure sensor 172. If the pressure within the generator 122 exceeds a predetermined level, the vent valve 162 is opened and an alarm is sounded. The generator 122 is also equipped with an overflow level sensor 174 that terminates the supply of chemicals to the tank 122 in the event the level sensor 170 fails.

If the pressure within the generator tank 122 is below the predetermined level, the sterilant/disinfectant generation process is continued and pumps 176 and 178 are activated. Pump 176 causes a mixture of chlorine dioxide and air to be circulated about a closed loop between the generator 122 and the sterilliation tank 124. As the mixture of air and chlorine dioxide passes through the sterilization tank 124, a significant portion of the chlorine dioxide gas dissolves in the water within the sterilization tank 124. Consequently, the concentration of chlorine dioxide within the sterilization tank gradually increases as chlorine dioxide is transferred from the generator 122 to the water within the sterilization tank 124.

The pump 178 causes the water from the tank 124 to flow along a closed loop between the tank 124 and the concentration sensor 126. Consequently, the concentration monitor 126 continuously monitors the concentration of chlorine dioxide that is dissolved in the water within the sterilization tank 124. When the chlorine dioxide concentration within the sterilization tank 124 reaches a predetermined level as sensed by the concentration monitor 126, pumps 176 and 178 are deactivated and valve 152 is opened.

By opening valve 152, a small amount of water is allowed to flow directly from the water supply 132 past the concentration monitor 126. The concentration monitor 126 takes a verification reading of the water to verify that the concentration monitor 126 is operating properly. If the reading is proper, then valve 152 is closed. If the reading indicates that the concentration monitor 126 is not operating properly, an alarm will sound.

Once a sterilant/disinfectant (hereinafter "sterilant") having a predetermined concentration of chlorine dioxide has been generated in the sterilization tank 124, the sterilant is ready to be used. In this regard, objects such as medical instruments can be sterilized or disinfected directly within the sterilization tank 124. Alternatively, the sterilant from the sterilization tank 124 can be dispensed to a remote sterilization/disinfection location. Before delivering the sterilant to the remote location, the temperature sensor 158 again verifies the temperature of the sterilant. Additionally, if the sterilant is not being used immediately after the sterilant has been generated, pumps 176 and 178 are reactivated to cause additional chlorine dioxide transfer in order to supplement the concentration of chlorine dioxide within the sterilization tank 124.

To dispense the sterilant from the sterilization tank 124, dispensing valve 180 and vent valve 154 are concurrently opened. Next, pump 182 is activated causing the sterilant to be dispensed through the dispensing valve 180. The pump 182 continues to remove the sterilant from the sterilization tank 124 until drain level sensor 184 is activated. Once the tank 124 is empty, vent valve 154 and dispensing valve 180 are closed.

If it is not desired to dispense the sterilant through dispensing valve 180, the sterilant can also be pumped through valve 186 to either the drain 146 or back through the filters 136 and 138 and flow lines of the system 120 such that the system itself is sterilized.

After the chlorine dioxide within the generator 122 has been consumed, the remaining byproduct solution of chlorite, sodium chloride and water is drained from the chlorine dioxide generator 122. Specifically, vent valve 162 is opened and pump 188 is activated such that the residual solution is drained from the generator 122. The pump 188 is deactivated when drain level sensor 190 senses that the generator tank 122 is empty. Once the tank 122 is empty, the vent valve 162 is closed.

If desired, a rinse cycle can be utilized to wash any remaining residual material from the tank 122. To initiate the rinse cycle, valve 192 and vent valve 162 are opened. Valve 192 allows water from the water supply 132 to flow into the generator tank 122. The generator tank 122 fills to level sensor 170, and then valve 192 is closed The water is then drained from the generator tank 122 in the same manner described above with respect to the residual solution of chlorite, sodium chloride and water.

It will be appreciated that any of the systems or methods disclosed herein can be used for both sterilization and disinfection processes. Consequently, terms such as disinfectant and sterilant, or sterilization and disinfection are intended to be interchangeable for the purpose of this disclosure.

With regard to the foregoing description, it is to be understood that changes may be made in detail, especially in matters of chemical employed and the arrangement of the component parts. It is intended that the specification and the depicted aspects be considered exemplary only, with a true scope and spirit of the invention being indicated by the broad meaning of the following claims.

What is claimed is:

1. A method for generating a volume of liquid disinfectant/sterilant fluid having a first concentration of chlorine dioxide, the method comprising:
   generating chlorine dioxide gas at a source of chlorine dioxide gas;
   transferring the chlorine dioxide gas from the source of chlorine dioxide gas to a separate disinfectant/sterilant chamber containing a liquid solvent;

monitoring the concentration of chlorine dioxide in the liquid solvent within the disinfectant/sterilant chamber; and discontinuing the transfer of chlorine dioxide gas to the disinfectant/sterilant chamber when the concentration of chlorine dioxide within the liquid solvent reaches the first concentration.

2. The method of claim 1, wherein the concentration of chlorine dioxide in the liquid solvent within the disinfectant/sterilant chamber is continuously monitored as the chlorine dioxide gas is transferred from the source of chlorine dioxide gas to the disinfectant/sterilant chamber.

3. The method of claim 1, wherein the concentration of chlorine dioxide in the liquid solvent within the disinfectant/sterilant chamber is monitored by using a light source and a photocell.

4. The method of claim 1, wherein the concentration of chlorine dioxide in the liquid solvent within the disinfectant/sterilant chamber is monitored by circulating the liquid solvent in a closed loop between the disinfectant/sterilant chamber and a concentration monitor.

5. The method of claim 1, wherein the liquid solvent is selected from a group consisting of water, alcohols, organic solvents and chlorinated solvents.

6. The method of claim 1, wherein the chlorine dioxide is generated by reacting a chlorite with an acid.

7. The method of claim 6, wherein the chlorite is sodium chlorite, and the acid is hydrochloric acid.

8. The method of claim 1, wherein the chlorine dioxide is circulated in a closed loop between the source of chlorine dioxide and the disinfectant/sterilant chamber.

9. The method of claim 4, wherein the concentration monitor includes a transparent chamber through which the liquid solvent flows, the transparent chamber being positioned between a light source for directing light through the transparent chamber, and a photocell for measuring the intensity of the light passing through the transparent chamber.

10. A method for disinfecting/sterilizing a medical instrument comprising:

generating a supply of chlorine dioxide gas at a source of chlorine dioxide gas;

transferring the chlorine dioxide gas from the source of chlorine dioxide gas to a separate disinfectant/sterilant chamber containing a liquid solvent;

monitoring the concentration of chlorine dioxide in the liquid solvent within the disinfectant/sterilant chamber;

discontinuing the supply of chlorine dioxide gas to the disinfectant/sterilant chamber when the concentration of chlorine dioxide within the liquid solvent contained in the disinfectant/sterilant chamber reaches a first concentration; and disinfecting/sterilizing the medical instrument within the liquid solvent contained in the disinfectant/sterilant chamber.

11. The method of claim 10, wherein the concentration of chlorine dioxide in the liquid solvent is continuously monitored as the chlorine dioxide is transferred from the source of chlorine dioxide gas to the disinfectant/sterilant chamber.

12. The method of claim 10, wherein the concentration of chlorine dioxide in the liquid solvent contained in the disinfectant/sterilant chamber is monitored by using a light source and a photocell.

13. The method of claim 10, wherein the chlorine dioxide is circulated in a closed loop between the source of chlorine dioxide gas and the disinfectant/sterilant chamber.

14. An apparatus for generating a volume of disinfectant/sterilant comprising:

a chlorine dioxide gas generator;

a disinfectant/sterilant chamber;

a fluid flow path for transferring chlorine dioxide gas from the chlorine dioxide gas generator to the disinfectant/sterilant chamber;

a source of liquid solvent for filling the disinfectant/sterilant chamber with a liquid solvent;

a concentration monitor for monitoring the concentration of chlorine dioxide within the liquid solvent contained in the disinfectant/sterilant chamber; and control circuitry interfacing with the concentration monitor for terminating the transfer of chlorine dioxide to the disinfectant/sterilant chamber when the concentration of chlorine dioxide within the liquid solvent reaches a first level.

15. The apparatus of claim 14, wherein the concentration monitor is arranged and configured to continuously monitor the concentration of chlorine dioxide in the liquid solvent contained in the disinfectant/sterilant chatnber as the chlorine dioxide gas is transferred to the disinfectant/sterilant chamber.

16. The apparatus of claim 14, wherein the concentration monitor includes a light source and a photocell.

17. The apparatus of claim 14, wherein the chlorine dioxide gas generator includes a source of sodium chlorite, and a source of hydrochloric acid.

18. The apparatus of claim 14, wherein the fluid flow path for transferring chlorine dioxide gas to the disinfectant/sterilant chamber is arranged in a closed loop between the generator and the disinfectant/sterilant chamber.

19. The apparatus of claim 14, wherein the concentration monitor includes a transparent chamber in fluid communication with the disinfectant/sterilant chamber, the transparent chamber being positioned between a light source for directing light through the transparent chamber, and a photocell for measuring the intensity of the light passing through the transparent chamber.

20. An apparatus for generating a volume of disinfectant/sterilant comprising:

generating means for generating chlorine dioxide gas;

a disinfectant/sterilant chamber;

means for transferring chlorine dioxide gas from the generating means to the disinfectant/sterilant chamber;

means for delivering a volume of liquid solvent to the disinfectant/sterilant chamber;

monitoring means for monitoring the concentration of chlorine dioxide within the volume of liquid solvent contained in the disinfectant/sterilant chamber; and means for terminating the transfer of chlorine dioxide to the disinfectant/sterilant chamber when the concentration of chlorine dioxide within the volume of liquid solvent reaches a first level.

* * * * *